United States Patent
Wilson et al.

(10) Patent No.: US 7,027,559 B2
(45) Date of Patent: Apr. 11, 2006

(54) METHOD AND APPARATUS FOR GENERATING X-RAY BEAMS

(75) Inventors: Colin Richard Wilson, Schenectady, NY (US); Amy Linsebigler Smentkowski, Clifton Park, NY (US); Lembit Salasoo, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 8 days.

(21) Appl. No.: 10/732,840

(22) Filed: Dec. 10, 2003

(65) Prior Publication Data

US 2004/0120462 A1 Jun. 24, 2004

Related U.S. Application Data

(63) Continuation-in-part of application No. 09/682,494, filed on Sep. 7, 2001, now abandoned.

(51) Int. Cl.
*H01J 35/30* (2006.01)

(52) U.S. Cl. .......... 378/137; 378/138; 378/144
(58) Field of Classification Search ......... 378/137, 378/143, 144, 138, 119, 121, 125, 135, 136
See application file for complete search history.

(56) References Cited

U.S. PATENT DOCUMENTS

| 4,075,489 | A | | 2/1978 | Neal et al. |
| 4,685,118 | A | | 8/1987 | Furbee et al. |
| 5,029,195 | A | * | 7/1991 | Danos ............... 378/121 |
| 5,828,727 | A | | 10/1998 | Schild |
| 6,052,434 | A | | 4/2000 | Toth et al. |
| 6,438,207 | B1 | * | 8/2002 | Chidester et al. .......... 378/138 |

* cited by examiner

Primary Examiner—Edward J. Glick
Assistant Examiner—Elizabeth Keaney
(74) Attorney, Agent, or Firm—Jason K. Klindtworth; Jean K. Testa

(57) ABSTRACT

A method and apparatus for generating x-ray beams are described. In one embodiment, the method includes operating a cathode to operating a cathode to generate an electron beam, directing the electron beam from the cathode through a selectable shaped aperture in an accelerating electrode, and impinging the electron beam at a low angle on an anode surface to form a focal spot on the anode surface.

11 Claims, 3 Drawing Sheets

METHOD AND APPARATUS FOR GENERATING X-RAY BEAMS

This application is a Continuation-in-Part of patent application Ser. No. 09/682,494, filed Sep. 7, 2001, abandoned.

BACKGROUND OF THE INVENTION

This invention relates generally to x-ray generating equipment, and more particularly to methods and apparatus for maintaining an electron beam incident angle and focus on an x-ray target anode.

In medical x-ray imaging, an x-ray tube is utilized for generating x-ray beams that pass through an object being imaged. More specifically, an x-ray source projects a fan-shaped beam that is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at a detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged, so the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent to the scintillator.

Known x-ray tubes include a cathode aligned with a rotating target anode. An electron beam generated at a cathode emitter is directed towards the anode and forms a focal spot on an anode surface. As a result, x-ray beams are emitted from the anode.

The shape and focus of the electron beam emitted from the cathode emitter are defined by the cathode. In spite of the shaping and focusing within the cathode, as the beam travels to the anode, electric fields within the x-ray tube can accelerate the electrons and possibly even deflect and defocus the beam. If the electron beam does not have the desired shape and focus, the resulting x-ray beam also will lack such characteristics. As a result, the image quality of an image generated based on projection data collected utilizing such x-ray beams may not be as high as desired.

BRIEF SUMMARY OF THE INVENTION

In one aspect, a method for generating an x-ray beam is provided. The method comprises the steps of operating a cathode to generate an electron beam, directing the electron beam from the cathode through a selectable shaped aperture in an accelerating electrode, and impinging the electron beam at a low angle on an anode surface to form a focal spot on the anode surface.

In a second aspect, an x-ray source is provided and the source comprises a cathode for generating an electron beam, an accelerating electrode comprising a selectable shaped aperture through which the electron beam from the cathode passes, and an anode positioned so that the electron beam impinges thereon at a low angle.

DETAILED DESCRIPTION OF THE INVENTION

Various embodiments of anode and cathode assemblies are described herein. Although such assemblies are sometimes described in the context of a computed tomography (CT) machine, and more specifically, a third generation CT machine, such assemblies are not limited to practice in such CT machines and can be utilized in other applications as well. Therefore, the description of such assemblies in the context of CT machines is exemplary only.

Figure 1:
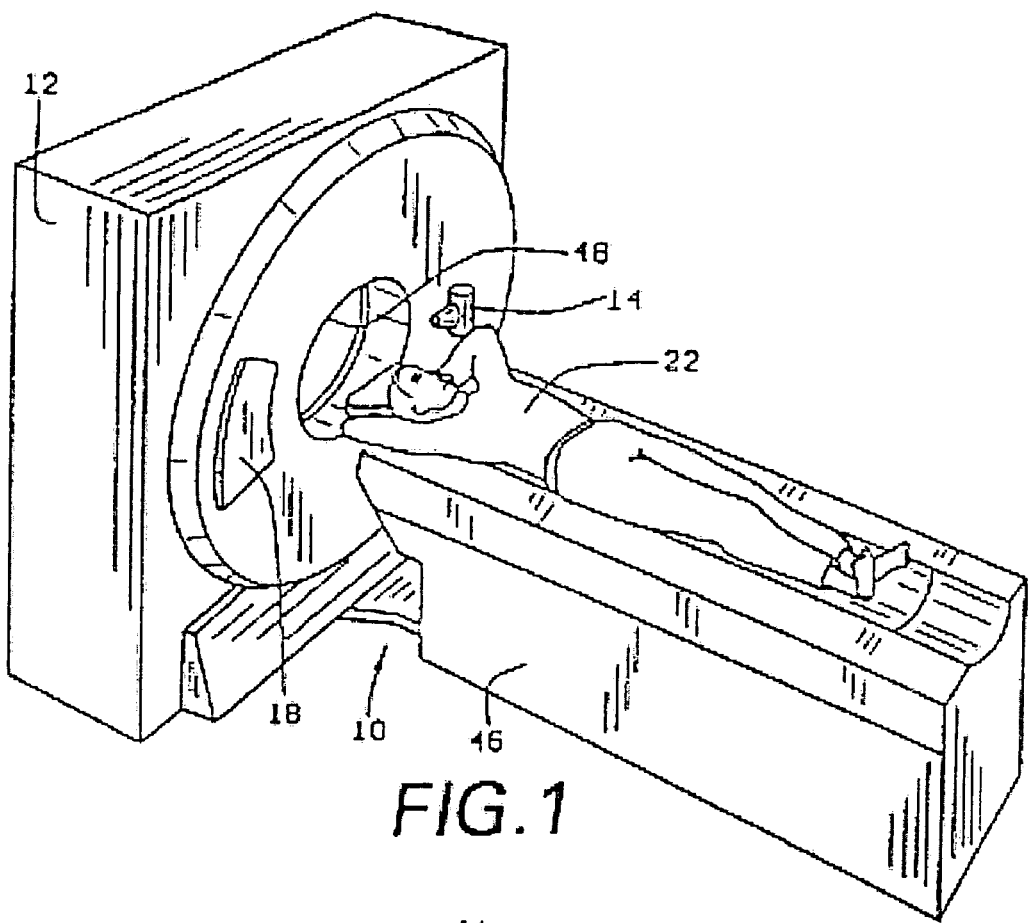
FIG. 1 is a pictorial view of a CT imaging system.
Figure 2:
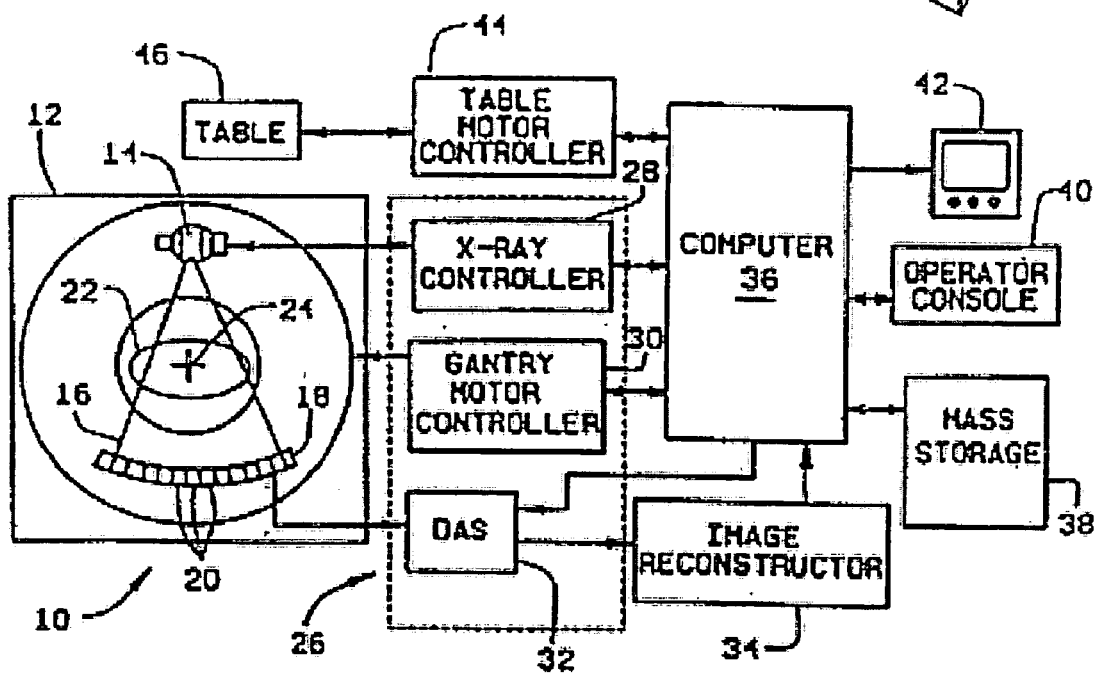
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
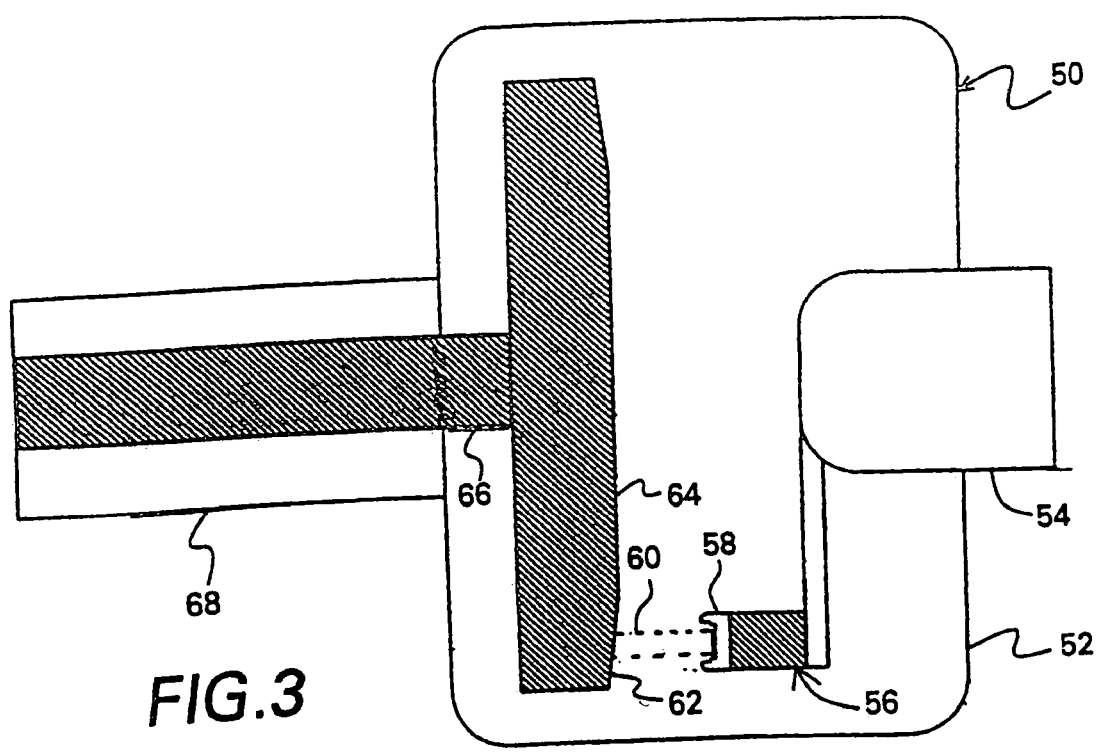
FIG. 3 is a schematic illustration of an x-ray tube; and,
FIG. 4 is a schematic illustration of an x-ray source assembly including an accelerating electrode.

FIG. 3 is a schematic illustration of an x-ray tube 50. Tube 50 includes a glass or metal envelope 52 which at one end has a cathode support 54 sealed into it. The electron emissive filament of a cathode 56 is mounted on insulators located in a focusing cup 58 which focuses an electron beam 60 against a beveled annular focal track area 62 of a rotating x-ray target 64. Target 64 is supported on a rotor shaft 66 that extends from a rotor assembly 68.

During operation, a rotating magnetic field is induced in the rotor of assembly 68 to cause rotor shaft 66 to rotate. In addition, electron beam 60 is emitted from cathode cup 58 and is focused on beveled annular focal track area or surface 62 of x-ray target 64. The electrons of beam 60 collide with anode 64 and as a result, x-ray beams are generated. A focal spot is formed on anode surface 62 by electron beam 60, and the x-ray beams emanate from the focal spot. The x-ray beams are through a window in envelope 52 and pass through an object being imaged, such as a patient.

As explained above, the shape and focus of the electron beam emitted from the cathode emitter are defined by the cathode, e.g., by the cathode filament. As the beam travels to the anode, however, electric fields within the x-ray tube can accelerate the electrons and possibly even deflect and defocus the beam. Such deflection and defocusing of the electron beam adversely impacts generation of a desired x-ray beam.

Figure 4:
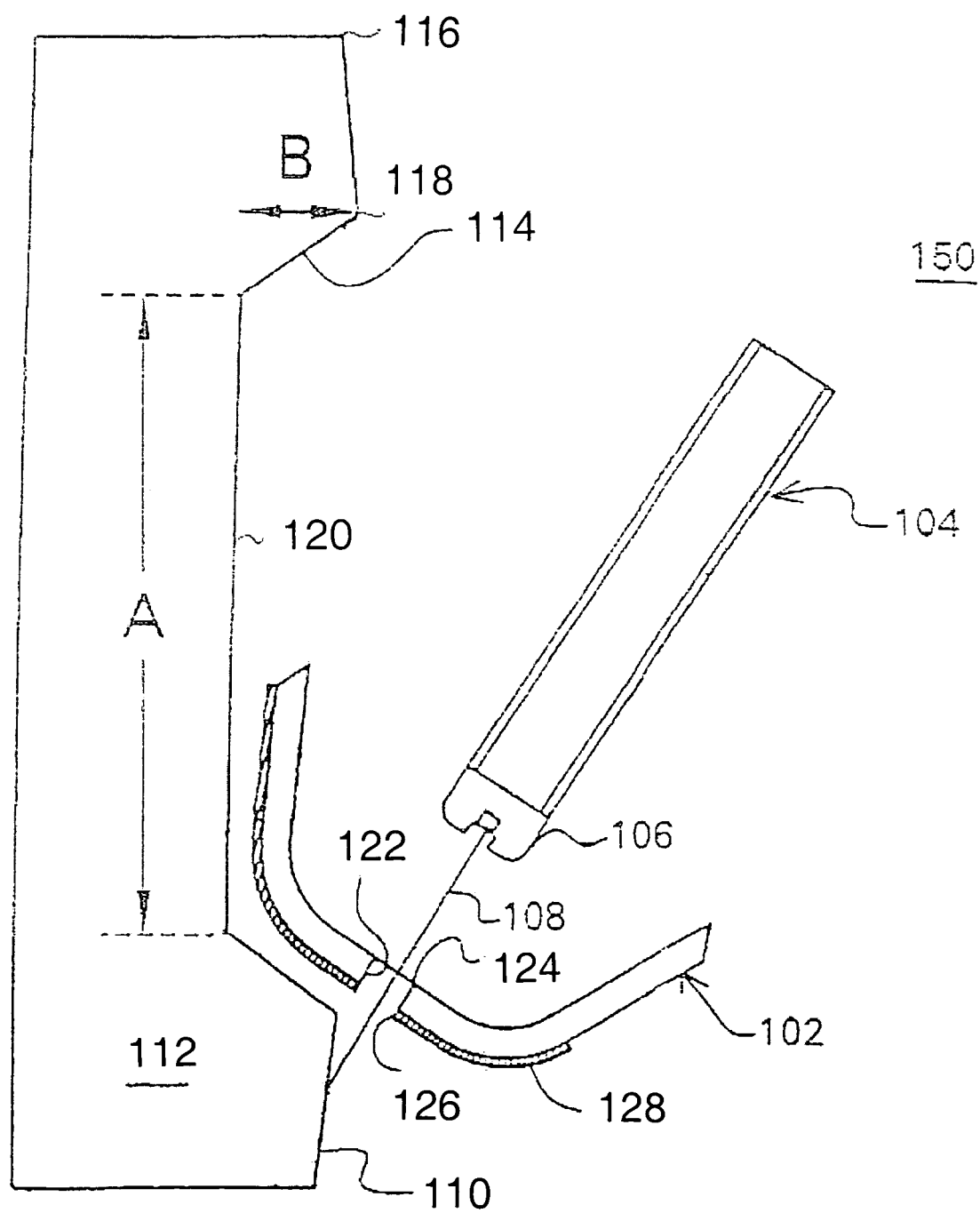

FIG. 4 is a schematic illustration of an exemplary x-ray source assembly 150 including an accelerating electrode 102. More specifically, an electron gun 104 including a cathode cup 106 is positioned to emit an electron beam 108 that impinges on a beveled surface 110 of an anode 112. Cathode cup 106, in the exemplary embodiment, contains numerous filaments selectable to provide different focal spot sizes and/or shapes. In an exemplary embodiment, cathode cup 106 and/or the filaments have a concave shape to facilitate focusing of the resulting electron beam on anode 112 as well as to reduce sensitivity of gun 104 to motion.

Target anode 112 is of a disk shape in one exemplary embodiment, and the shape of anode 112 is defined by an outer periphery 116, an inner periphery 118 and a central recess 120 as shown in FIG. 4. The central recess 120 houses the accelerating electrode 102. The outer periphery 116 includes a beveled target surface 110, which is a focal spot region. The accelerating electrode 102 is positioned such that it is close to the focal spot region. Housing the accelerating electrode 102 in the central recess 120 allows the beam path to be minimized, which leads to a generating a better focal spot. Anode 112 also includes a cut-out center portion 114 which also facilitates locating accelerating electrode 102 near the focal spot of electron beam 108. By selecting dimensions A and B of anode 112, a shorter or longer electron beam path from electron gun 104 to the focal spot on anode 112 is provided. When placed in operation, the electron beam 108 generated from the cathode 104 is directed through a selectable shaped aperture 116 in the accelerating electrode 102 and impinges the anode 112 at a low angle. The low angle, the beam 108 makes at the anode 112 surface is at most about twenty degrees. It would be appreciated by one skilled in the art that the low angle impact of the beam 108 leads to better energy distribution and allows the x-ray tube to be operated at higher power levels. Also the thermal stresses on the anode are reduced due to the low angle impact of the beam 108. It will also be appreciated by those skilled in the art that anode 112 can have many different shapes and is not limited to the exemplary shape illustrated in FIG. 4.

Accelerating electrode 102 is positioned to reduce the electric fields that might otherwise be present between accelerating electrode 102 and target 112, i.e., a space where the electrons of electron beam 108 from gun 104 experience very little or no forces that can perturb their motion. Generally, accelerating electrode 102 provides that the region or area between accelerating electrode 102 and target 112 has a low electric field so that the effects on the transiting electron beam are not of significance. More specifically, in one example, accelerating electrode 102 is maintained at a positive potential with respect to the cathode of gun 104 thus imparting acceleration to electrons of electron beam 108 in the direction away from the cathode.

Accelerating electrode 102 includes an opening or aperture 122, and electron beam 108 from gun 104 passes through opening 122 and impinges on anode 112. The shape of aperture 122 at input 124 and at output 126, or both, can be selected to provide focusing and control of an incident angle, i.e., the angle at which beam 108 impinges on anode 112. In addition, removable inserts can be located in aperture 122 to provide for an easy change in focusing/incident angle, replacement, and/or reconditioning.

Accelerating electrode 102 can be cooled by convection cooling. Specifically, cooling fluid can be supplied to electrode 102 for maintaining a temperature of electrode 102 with a pre-set range. To facilitate cooling, electrode 102 can include fins or have a geometric shape which facilitates cooling. Electrode 102 also can be coupled to the x-ray source frame and cooled by cooling fluid that circulates in the frame casing.

Accelerating electrode 102 can also function as an electron collector. Specifically, accelerating electrode 102 can have a geometric shape to facilitate capturing back scattered electrons. The actual shape selected depends on the trajectories of the back scattered electrons. Surfaces which collect the majority of the back scattered electrons can be coated with a low atomic number material 128 such as carbon (e.g., graphite) to limit spurious radiation influences, as shown in FIG. 4.

Accelerating electrode 102 also can be configured to intercept only a low fraction of the electron back scattered flux and/or thermal radiation flux. As a result, accelerating electron heating is not as great as when accelerating electrode 102 is specifically configured to capture back scattered electrons. Again, the specific geometric shape depends on the trajectories of the back scattered electrons.

In addition, accelerating electrode 102 can be operated at ground potential or raised to a negative or positive potential. The specific circuit arrangement for providing the desired potential depends, of course, on the x-ray tube arrangement. Controlling the potential of accelerating electrode 102 facilitates focusing electron beam 108 from gun 104.

In a bi-polar configuration, accelerating electrode can be located close to target anode, i.e., accelerating electrode and anode are separated only by a distance required to maintain mechanical clearance between the rotating anode and the stationary accelerating electrode. The anode and electrode can be located closely together in such a configuration because both the anode and the electrode are at a same voltage and require no dielectric standoff. To lower localized accelerating electrode hot spots, the accelerating electrode surfaces facing the focal spot on the target anode can be located at a greater distance than required for mechanical and dielectric clearance in order to avoid concentration of electron back scatter and/or thermal radiation flux.

While the invention has been described in terms of various specific embodiments, those skilled in the art will recognize that the invention can be practiced with modification within the spirit and scope of the claims.

What is claimed is:

1. A method for generating an x-ray beam, said method comprising the steps of:
   operating a cathode to generate an electron beam;
   directing the electron beam from the cathode through a selectable shaped aperture in an accelerating electrode, wherein the accelerating electrode is positioned in a central recess of an anode surface; and
   impinging the electron beam at an acute angle on an the anode surface to form a focal spot on the anode surface.

2. The method of claim 1, wherein the acute angle is at most about twenty degrees.

3. The method of claim 1 further comprising forming the focal spot on an outer periphery of the anode surface.

4. An x-ray source comprising:
   a cathode for generating an electron beam;
   an accelerating electrode positioned in a central recess of an anode surface, the accelerating electrode comprising a selectable shaped aperture through which the electron beam from said cathode passes; and
   an anode positioned so that the electron beam impinges thereon at an acute angle.

5. The x-ray source of claim 4, wherein the acute angle is at most about twenty degrees.

6. The x-ray source of claim 4, wherein the anode comprises a disk shape, the disk shape being defined by an outer periphery, an inner periphery and the central recess.

7. An imaging system comprising a gantry, a detector and an x-ray source coupled to said gantry, said x-ray source configured for radiating an x-ray beam along an imaging plane toward said detector, said x-ray source comprising a cathode for generating an electron beam, an accelerating electrode positioned in a central recess of an anode surface, the accelerating electrode comprising a selectable shaped aperture through which the electron beam from said cathode passes, and an anode positioned so that the electron beam impinges thereon at a acute angle.

8. The imaging system of claim 7, wherein the acute angle is at most about twenty degrees.

9. The imaging system of claim 7, wherein the anode comprises a disk shape, the disk shape being defined by an outer periphery, an inner periphery and the central recess.

10. An x-ray source comprising:
    means for generating an electron beam,
    means for accelerating electrons in said electron beam away from said generating means, wherein the means for accelerating electrons is located in a central recess of an anode surface, and
    means for generating x-ray beams when said electron beam impinge thereon at an acute angle.

11. The x-ray source of claim 10, wherein the acute angle is at most about twenty degrees.

* * * * *

UNITED STATES PATENT AND TRADEMARK OFFICE
CERTIFICATE OF CORRECTION

PATENT NO. : 7,027,559 B2
APPLICATION NO. : 10/732840
DATED : April 11, 2006
INVENTOR(S) : Colin Richard Wilson, Amy Linsebigler Smentkowski and Lembit Salasoo It is certified that error appears in the above-identified patent and that said Letters Patent is hereby corrected as shown below:

Col. 5 lines 1-10
Claim 1 should read as follows:

1. A method for generating an x-ray beam, said method comprising the steps of:

operating a cathode to generate an electron beam;

directing the electron beam from the cathode through a selectable shaped aperture in an accelerating electrode, wherein the accelerating electrode is positioned in a central recess of an anode surface; and impinging the electron beam at an acute angle on the anode surface to form a focal spot on the anode surface.

Signed and Sealed this

Fifth Day of September, 2006

JON W. DUDAS
*Director of the United States Patent and Trademark Office*